(12) United States Patent
Mahe et al.

(10) Patent No.: US 10,744,072 B2
(45) Date of Patent: Aug. 18, 2020

(54) COSMETIC COMPOSITION FOR ORAL ADMINISTRATION FOR REINFORCING THE SKIN BARRIER

(71) Applicant: NUTRICOS Technologies, Clichy (FR)

(72) Inventors: Yann Mahe, Ste Genevieve des Bois (FR); Carole Bru, Courbevoie (FR)

(73) Assignee: NUTRICOS TECHNOLOGIES, Clichy (FR)

( * ) Notice: Subject to any disclaimer, the term of this patent is extended or adjusted under 35 U.S.C. 154(b) by 0 days.

(21) Appl. No.: 15/542,793

(22) PCT Filed: Jan. 15, 2016

(86) PCT No.: PCT/EP2016/050794
§ 371 (c)(1),
(2) Date: Jul. 11, 2017

(87) PCT Pub. No.: WO2016/113402
PCT Pub. Date: Jul. 21, 2016

(65) Prior Publication Data
US 2017/0367935 A1    Dec. 28, 2017

(30) Foreign Application Priority Data
Jan. 16, 2015 (FR) ...................... 15 50386

(51) Int. Cl.
| A61K 8/02 | (2006.01) |
| A61K 8/19 | (2006.01) |
| A61K 8/31 | (2006.01) |
| A61Q 19/08 | (2006.01) |
| A61Q 19/00 | (2006.01) |

(52) U.S. Cl.
CPC ............... *A61K 8/02* (2013.01); *A61K 8/19* (2013.01); *A61K 8/31* (2013.01); *A61Q 19/00* (2013.01); *A61Q 19/08* (2013.01); *A61K 2800/522* (2013.01); *A61K 2800/92* (2013.01)

(58) Field of Classification Search
None
See application file for complete search history.

(56) References Cited

U.S. PATENT DOCUMENTS

| 2002/0132800 | A1* | 9/2002 | Popp ................ A23L 33/00 514/168 |
| 2009/0220619 | A1* | 9/2009 | Cotter ............... A23L 33/105 424/638 |
| 2011/0008308 | A1* | 1/2011 | Taylor ............... A61K 8/0216 424/94.1 |
| 2012/0027897 | A1* | 2/2012 | Innocenzi .......... A23L 2/02 426/231 |
| 2012/0184506 | A1* | 7/2012 | Bonnet ............... A61K 8/41 514/54 |
| 2016/0030311 | A1* | 2/2016 | Sanguinetti ........ A61Q 19/08 424/94.1 |

FOREIGN PATENT DOCUMENTS

| WO | WO-02/054890 A2 | 7/2002 |
| WO | WO-02/054890 A3 | 7/2002 |
| WO | WO-2009/115769 A1 | 9/2009 |
| WO | WO-2015/062615 A1 | 5/2015 |

OTHER PUBLICATIONS

Tomatoes and Skin Protection—BBC 2013 (Year: 2013).*
Sun Allergy photosensitivity—Vitamin Life 2011 (Year: 2011).*
World's Healthiest Foods, obtained online at: http://www.whfoods.com/genpage.php?tname=foodspice&dbid=44, downloaded on Feb. 18, 2019. (Year: 2019).*
Salamone, obtained online at: http://mauriziosalamone.blogspot.com/2011/10/nnanganese-and-skin-health.htnnl, pp. 1-3. (Year: 2011).*
Darvin et al., European Journal of Pharmaceutics and Biopharmaceutics, 69, pp. 943-947. (Year: 2008).*
Pandel et al., ISRN Dermatology, pp. 1-11. (Year: 2013).*

* cited by examiner

*Primary Examiner* — Abigail Vanhorn
(74) *Attorney, Agent, or Firm* — Polsinelli PC

(57) ABSTRACT

This invention relates to the cosmetic use by oral route of a combination of lycopene and manganese to prevent a decrease of and/or reinforce the barrier function of the skin.

15 Claims, No Drawings

COSMETIC COMPOSITION FOR ORAL ADMINISTRATION FOR REINFORCING THE SKIN BARRIER

CROSS-REFERENCE TO RELATED APPLICATIONS

This application is a National Phase filing under 35 U.S.C. § 371 of International Application No. PCT/EP2016/050794, filed Jan. 15, 2016, which claims priority to Application No. 15 50386, filed in France on Jan. 16, 2015. The entire contents are incorporated herein by reference.

This invention relates to a composition for oral administration intended to reinforce the skin barrier The epidermis if the first interface between an organism and the external environment. More particularly the cornified envelope (CE: stratum corneum) is a specialized structure that represents the first defense of the skin. The obtaining of this first skin barrier corresponds to a process of terminal differentiation of epidermal keratinocytes. This process results in the formation of a superficial layer coming from the aggregation of dead and flattened keratinocyte cells of which the cytosol, after the loss of the functional core, was replaced with a matrix of aggregates of insoluble proteins and lipids.

The skin therefore forms a barrier against external aggression, in particular chemical or mechanical, and as such a certain number of defense reactions against environmental factors (climate, ultraviolet rays, etc.) occur at its level. This property is called the barrier function.

An alteration of the skin barrier can occur in the presence of external aggressions of the irritant agent type (detergents, acids, bases, oxidants, reducers, concentrated solvents, toxic gases or fumes), mechanical stress (friction, impacts, abrasion, pulling off of the surface, projection of dust, particles, shaving or depilation), thermal or climate imbalances (cold, drought, radiation), xenobiotic (undesirable microorganisms, allergens) or internal aggressions of the psychological stress type.

This alteration of the skin barrier can in particular result in cutaneous discomfort, sensory phenomena and in particular unpleasant phenomena. The subject can then feel a sensation of cutaneous discomfort that can manifest itself in the form of tingling, tautness, heating or itching.

These feelings of cutaneous discomfort are more frequent in the most exposed zones of the organism, in particular the hands, feet and the face.

They can occur in particular on zones subjected to certain daily gestures of hygiene or gestures frequently repeated such as shaving, depilation, debridement by toiletry products or household products, the application of adhesives (bandages, patches) or in the case of sports, professional gestures or simply linked to lifestyle and the use of clothing, tools or equipment that generates local friction. They can also by amplified by psychological stress.

These feelings of discomfort also appear in the case of dry skin.

There is therefore a substantial need for compositions that make it possible to prevent a decrease of and/or to reinforce the skin barrier function, in particular to prevent and/or decrease the sensations of cutaneous discomfort, tingling, tautness, heating or itching, or that make it possible to increase the state of hydration of the skin.

The barrier function of the skin can also be altered following aesthetic treatments, such as surface treatments of the epidermis that implement for example chemical peeling agents that comprise glycolic or lactic acids, dermabrasion or laser resurfacing. In these conditions, there is a substantial need to accelerate the reconstitution of a protective surface barrier in order to provide better and faster protection of new skin.

Loricrin represents most of the mass of the CE and the rest of the proteins include involucrin, small prolin rich proteins (SPRR) as well as late cornified envelope proteins (LCE). Gene Knockout studies in preclinical models have shown that an experimental total deficiency in Loricrin in the epidermis in utero, was offset by the epidermal overexpression of SPRR2D and SPRR2H and could as such make it possible, after a short adaptation phase, to maintain a viable cutaneous barrier function in utero. This result suggests that SPRRs can provide an essential function as a compensating substitution for maintaining the skin barrier function (Huebner et al., Dev Cell. 2012 Dec. 11; 23(6): 1238-1246).

More particularly, few studies have been done on the family of SPRRs and it has recently been identified and characterized in the epidermis as being key for the formation of the protective barrier function of the skin, the quality of its mechanical properties and its surface protection with regards to a large family of endogenous and external stimuli (Cabral et al., J. Biol. Chem. 2001, 276:19231-19237). Type-2 SPRRs are more particularly expressed in the stratum *Granulosum* (Katou et al., Br J Dermatol., 2003; 148:898-905).

The regulation of the expression of SPRRs is under the control of the ubiquitous factor Nrf2 which is the key transcriptional regulator for the antioxidant response. After stress, in particular UV or xenobiotics linked stress and which leads to the generation of undesirable radicals (ROS) in the skin, Nrf2 activates as compensation cytoprotective antioxidant genes among which SPRRs. SPRRs can also be induced in the stratum corneum as a response to stress other than UV, in particular in the conditions of healing (Huebner et al., Dev Cell. 2012 Dec. 11; 23(6): 1238-1246).

Moreover, in light of their particular content in cysteine, it appears that SPRRs of the cornified envelope can provide a direct function of the chemical neutralization of reactive oxygen species (ROS) on the surface of the skin by polymerizing in the stratum corneum (Vermeij et al., J Invest Dermatol. 2011 131(7):1435-41). Knowing that ROS have been considered since the 1950's as the key factors that maintain the progression of the aging of skin the interest is understood that there is in activating the natural production of these skin-protecting agents in order to neutralize on a daily basis the effects of acute radical stress such as those linked to healing in progress or excessive exposure to the sun but also those with much less noise such as those linked to pollutants, xenobiotics and linked to the endogenous metabolism in order to limit their deleterious activity of and/or the duration of their undesirable effect on the skin.

As such it appears interesting to favor the expression of SPRRs before an exposure of the skin to stress in order to prepare it. Surprisingly, the inventors have shown that administering a specific combination of lycopene and manganese made it possible to increase, in a synergic manner, the keratinocytes expression of SPRRs and in particular of SPRR2D. Thanks to the increase in the keratinocytes expression of SPRRs, the skin barrier function can be reinforced.

This invention therefore relates to the cosmetic use by oral route of a combination of lycopene and manganese as an agent to prevent a decrease of and/or to reinforce the barrier function of the skin.

"Prevent a decrease of the barrier function of the skin" means here to prevent any alteration of said barrier function below its natural level of effectiveness and which result in initiating the manifestation of one or more cutaneous discomforts.

"Reinforce the barrier function of the skin" here means to improve the barrier function of the skin.

This invention also relates to the cosmetic use by oral route of a combination of lycopene and manganese as an agent to reinforce the protection of the skin with regards to external aggressions.

The combination according to the invention can in particular be used to prevent and/or to reduce a cutaneous discomfort of a skin, in particular induced by an exogenous stress of chemical, environmental, mechanical origin and/or an endogenous stress.

The combination according to the invention can be more particularly used to prepare the skin for an outside aggression.

"Environmental stress" means in particular acute radical stress such as those linked to excessive exposure to the sun (UVs), but also those with much less noise such as those linked to pollutants or to xenobiotics.

Cutaneous discomfort can in particular be characterized by tautness, tingling, heating and/or itching.

According to an embodiment, the combination according to the invention can be used in a subject having a skin chosen from among fragile skin, weakened skin and/or aggressed skin.

The combination according to the invention can also be used to improve the state of hydration of the skin.

According to an embodiment, the combination according to the invention can be used in a subject having dry skin.

According to another embodiment, the combination according to the invention can be used in a subject having healthy skin, in particular subjected to or which might be subjected to external aggressions.

The combination according to the invention makes it possible more particularly to protect the skin with regards to friction, more particularly with regards to the formation of blisters.

According to an embodiment of the invention, the lycopene and the manganese of the combination act in a synergic manner on the expression of SPRRs and in particular of SPRR2D.

"In a synergic manner" means a combination of characteristics of which the functional interaction produces a combined technical effect that goes beyond the sum of the technical effects that they produce individually. In the case of the invention, the combination of lycopene and manganese makes it possible to increase the expression of SPRRs and in particular of SPRR2D in a proportion exceeding the sum of the increase permitted by lycopene and manganese individually.

According to an embodiment of the invention, the combination comprises lycopene and manganese as the only active compounds.

According to a particular embodiment, the combination according to the invention is suitable for preparing the skin for aesthetic treatment conditions during which its barrier function is altered, such as surface treatments of the epidermis with chemical peeling agents that use glycolic or lactic acids, or dermabrasion and laser resurfacing.

The combination according to the invention can also be used as a solar preparer, in order to prepare the skin for exposure to the sun.

Lycopene is a natural pigment found in ripe fruit, especially in tomatoes. It belongs to the carotenoid family and its structure is close to that of β-carotene.

The role of lycopene in the ripening of fruit is known. Lycopene is used in compositions with a tanning activity for its role on the synthesis of melanin (WO 97/47278), in compositions intended for the treatment of the scalp and/or acne for its activity on 5α-reductase (JP-2940964), as an anti-radical agent (JP-A-8-283136) or is used in compositions intended to treat, in a preventive and/or curative manner, the cutaneous signs of aging (EP 1 090 628).

Lycopene used according to the invention can be of natural or synthetic origin.

Natural origin means lycopene, in a pure state or in a solution regardless of its concentration in said solution, obtained from a natural element such as for example a plant extract, particularly a tomato or a mushroom, particularly *Blakeslee trispora*.

Synthetic origin means lycopene, in a pure state or in a solution regardless of its concentration in said solution, obtained through chemical synthesis.

When lycopene is of a natural origin, it can be obtained from a living organism cultivated in vivo or from an in vitro culture. Cultivated in vivo, in particular for a plant, means any culture of the conventional type, i.e. in the ground, in the open air or in a greenhouse, or off the ground. Cultivated in vitro means all of the techniques known to those skilled in the art that make it possible to artificially obtain the product from a living organism or from a portion of the latter. Preferably, the lycopene used in the context of the invention comes from a lycopene-rich tomato extract. Lycopene can also come from melon, guava or grapefruit. Any extraction method known to those skilled in the art can be used to prepare the lycopene used according to the invention. Lycopene can be in an aqueous suspension. For this, cold or hot water-dispersible forms, can be used, such as those marketed by Lycored under the trade names Lyc-o-Mato CWD. According to an embodiment of the invention, lycopene is used in the form of a lycopene-rich tomato extract, prepared by Lycored, marketed under the trade name LycOMato constituted of an oleoresin extract containing for example from 6 to 10% pure lycopene. Any other more complex ingredient with a lycopene base can also be used to realize the invention. As such, a more complex ingredient means for example a primary composition comprising lycopene and a whey protein. This primary composition is in particular described in document WO 01/91588. This primary composition is also called lactolycopene. It has the interest of increasing the bioavailability of the lycopene and/or of being easily formulated in dietary supplements (bag, capsule, tablets, sugar-coated pill, soft capsule, etc.).

The quantity of lycopene that can be used according to the invention is of course according to the effect sought and can therefore vary greatly. In order to give an idea of magnitude, lycopene can be used in its pure state in a quantity that represents from 0.0001 to 50% by weight, preferably from 0.001 to 10% by weight, preferentially in a quantity representing from 0.02 to 5% by weight with respect to the total weight of the composition. Of course those skilled in the art, if lycopene is used in the form of a solution, a plant extract for example, know how to adjust the quantity of solution used in the composition so that the final quantity of lycopene in the composition is in accordance with the quantities that can be used defined hereinabove.

Manganese is a dietary element. Manganese has several valences (1 to 7), the di- and trivalent forms are those that are the most biologically active.

Manganese used according to the invention can have an ionic form and/or the form of isolated inorganic or organic salts and/or present in natural extracts, plants, such as walnut extract (*Juglans regia*), bacterial extract or a mixture thereof.

The manganese organic salts that can be used according to the invention can be a manganese salt of a carboxylic acid such as manganese gluconate, manganese carbonate, manganese acetate, manganese citrate, manganese oleate, manganese oxalate, manganese lineolate or manganese linolenate, or a manganese salt of a aliphatic dicarboxylic acid such as sebacic acid, seboric or azelaic acid or a mixture thereof.

Preferably, the manganese used in the context of the invention is in the form of an inorganic manganese salt. The inorganic manganese salts can be chosen from mineral salts such as manganese chloride, manganese borate, manganese nitrate, manganese phosphate, manganese sulfate or a mixture thereof. According to an embodiment of the invention, the manganese used in the context of the invention is used in the form of manganese sulfate. In order to give an idea of magnitude, manganese can be used in a quantity that represents from 0.0001 to 50% by weight, preferably from 0.001 to 10% by weight, preferentially in a quantity representing from 0.02 to 5% by weight with respect to the total weight of the composition.

The combination of lycopene and manganese is preferably in the form of a cosmetic composition or in the form of separate cosmetic compositions, comprising preferably a physiologically acceptable medium "Physiologically acceptable medium" means a medium that is compatible with an administration to a human subject, suited to the administration route of the composition, i.e. in the case of oral administration, a medium that is compatible with the digestive system and in the case of topical administration compatible with the skin, and/or mucous membranes and preferably compatible with damaged skin, and compatible with the form in which the composition is intended to be packaged, in particular solid or fluid at ambient temperature and atmospheric pressure.

Preferably, the lycopene and the manganese are present in the composition at a molar ratio of lycopene over manganese between 1/10 and 10/1, preferably between 1/5 and 5/1, and very preferably at a ratio 1/1.

According to a preferred embodiment, the combination used in the context of the invention is used in combination with further at least an additional agent that prevents a decrease of and/or that reinforces the skin carrier function. Such agents are well known to those skilled in the art.

The additional agents that are suitable for the invention can be chosen from vitamin D, lutein, probiotic *Lactobacillus paracasei* ST11, melanotropin modulators and in particular MSH alpha modulators.

According to a particular embodiment, the composition or compositions comprising the combination according to the invention furthermore comprises at least one additional ingredient chosen from solvents, thickeners or gelling agents in the aqueous phase or oily phase, coloring agents soluble in the medium of the composition, fillers, pigments, antioxidants (such as vitamin C), preservatives, perfumes, electrolytes, neutralizing agents, UV blocking agents, cosmetic and pharmaceutical active agents, and mixtures thereof.

The composition or compositions comprising the combination according to the invention is suited for oral administration.

Said composition for oral administration can in particular have the form chosen from soft capsules, banded capsules, gels, dry or liquid emulsions, tablets, powders to be diluted, orodispersible powders, oils or drinkable ampoules.

A composition used in the context of the invention can moreover be formulated with the usual excipients and components for such oral compositions or dietary supplements, namely in particular fatty and/or aqueous components, humectants, thickeners, preservatives, agents for texture, flavor and/or coating, and/or antioxidants.

The pH of a composition according to the invention, when it comprises at least one aqueous phase (e.g.: aqueous solutions, emulsions . . . ), is preferably between 4 and 9, preferably between 4 and 7, advantageously between 5 and 6, and in particular a pH of 5.5.

The amounts of the various constituents of the physiological environment of the composition according to the invention are generally those used in the fields considered. Furthermore, these compositions are prepared according to routine methods.

Preferably, the combination of lycopene and manganese is used as an active agent at an effective quantity, i.e. at a quantity that allows it to have the desired effect.

This invention also relates to a cosmetic method to prevent a decrease of and/or reinforce the barrier function of the skin, as defined hereinabove, comprising at least one step of administration, simultaneous, separate or sequential, to an individual, by oral route, of a combination of lycopene and of manganese such as defined hereinabove.

According to an embodiment, said lycopene and said manganese are administered in the form of the cosmetic composition or dietary supplement such as described hereinabove. According to a particular embodiment, said administration of the combination is daily for a period of 1 to 16 weeks.

The combination according to the invention can also be administered to an individual having a skin having clinical signs of a deficit of the skin barrier, for example having an atopic skin.

Indeed, in the case of experimentally-induced atopic dermatitis in preclinical models, a compensatory induction of expression of SPRR2D in the epidermis has been shown (Kypriotou et al., PLoS ONE, 2013, 8(7): e67869). The combination according to the invention, by inducing the expression of SPRR2D in keratinocytes, should therefore make it possible to limit the atopic eruption by reinforcing the protective quality of the stratum corneum.

This invention therefore also relates to a combination of lycopene and manganese such as defined hereinabove, for its simultaneous, sequential or separate use, by oral route, for the prevention of a decrease of and/or for the reinforcing of the barrier function of damaged skin, in particular of an atopic skin.

This invention also has for object a combination, preferably dermatological, comprising a combination of lycopene and manganese for its use by oral route for the prevention of a decrease and/or for the reinforcing of the barrier function of damaged skin, in particular of an atopic skin.

The combination according to the invention is then administered by oral route.

The examples hereinafter are given by way of illustration and are not intended to restrict the field of the invention.

EXAMPLES

Example 1: Analysis of the Synergic Effect of the Lycopene and Manganese Combination on the Expression of SPRR2D This example shows that the combination of lycopene and manganese makes it possible to increase in a synergic manner the gene expression of SPRR2D in human keratinocytes.

The effect of the lycopene and manganese was studied separately then in combination on the gene expression profile (RNAm) of human keratinocytes NHEK (normal human epidermal keratinocytes) per RT-qPCR. The results are presented in table 1.

A 24-well plate was seeded with keratinocytes then placed into culture for 24 hours. The culture medium was then replaced with the test medium comprising according to the cases 0 (negative control), one or two tested compounds. The cells were incubated in this test medium for 18 hours then washed and frozen at −80° C. Each condition was carried out in triplicate. Two samples of each triplicate were grouped together, then the RNAm was extracted therefrom using TriPure Isolation Reagent® according to the supplier's recommendations. The ADNc was synthesized via reverse transcription of total RNA by "Transcriptor Reverse Transcriptase" from Roche. Then a quantitative PCR was performed in the presence of a fluorophore. The incorporation of fluorophore in the amplified DNA was measured during the PCR cycles. Two genes were used as a reference (RPS28 ad GADPH), in order to standardize the results. As such the level of expression of the studied genes was compared to the average level of expression of these two reference genes for all of the conditions tested.

For this test, the source of lycopene is Lyc-o-Mato marketed by Lycored and the source manganese is manganese sulfate.

TABLE 1

Expression expressed as a percentage in relation to the conditions without added compound

|  | Lyc-o-Mato 10 µg/ml | Manganese Sulfate 10 µg/ml | Lyc-o-Mato 10 µg/ml + Manganese Sulfate 10 µg/ml |
|---|---|---|---|
| Control (GAPDH) | 98 | 96 | 100 |
| Control (RPS28) | 108 | 117 | 99 |
| SPRR2D | 511 | 106 | 1718 |

These results therefore show a synergic effect between the lycopene and the manganese on the expression of SPRR2D in vitro.

Example 2

Solar formula for administration by oral administration (tablets):

| | Trade name | Daily dose (mg/day) |
|---|---|---|
| Ingredients: | | |
| Lycopene | Lactolycopene 2% | 4 |
| Manganese | Manganese Sulfate Monohydrate, USP/EP, Low HM powder | 2.3 |
| Vitamin C | Ascorbic Acid 90% Granulation | 40 |
| Lutein | FloraGlo Lutein 10% CW/S-TG | 2 |
| Excipients: | | |
| Dicalcium phosphate dihydrate | Emcompress | 250 |
| Microcrystalline cellulose | Prosolv | 160 |
| Croscarmellose sodium | Vivasol GFLM | 20 |
| Silicon dioxide | ProSolv HD90 | 10 |
| Coloring agent | Opadry white | 40 |

Example 3

Formula for reinforcing the barrier function of the skin, for oral administration (capsules) comprising probiotic ST11

| | Trade name | Daily dose (mg/day) |
|---|---|---|
| Ingredients: | | |
| Lycopene | Lactolycopene 2% | 4 |
| Manganese | Manganese Sulfate Monohydrate, USP/EP, Low HM powder | 2.3 |
| Culture in powder of Lactobacillus paracasei ST11 | ST11 | 50 (contribution in ST11: min. 1E+09 cfu/d) |
| Excipients: | | |
| Colloidal silicon dioxide | Aerosil 200 Pharma | 5 |
| Corn flour | C*Gel LM 03411 | 200 |
| Magnesium stearate | Ligamed MF-2-V | 3 |

Example 4

Oral formula for reinforcing the protection of atopic skins between the phase of pharmacologic treatment and as such prolong the remission phases between atopic eruptions. The dosage is one tablet per day for 3 months.

| | Trade name | Daily dose (mg/day) |
|---|---|---|
| Ingredients: | | |
| Lycopene | Lactolycopene 2% | 4 |
| Manganese | Manganese Sulfate Monohydrate, USP/EP, Low HM powder | 2.3 |
| Excipients: | | |
| Dicalcium phosphate dihydrate | Emcompress | 250 |
| Microcrystalline cellulose | Prosolv | 250 |
| Croscarmellose sodium | Vivasol GFLM | 60 |
| Silicon dioxide | ProSolv HD90 | 17 |
| Colorants | Opadry white | 30 |

The invention claimed is:

1. A cosmetic method to reinforce the barrier function of the skin comprising at least one step of administering, simultaneously, separately or sequentially, to an individual by oral route a combination of lycopene and of manganese as agents to reinforce the barrier function of the skin, wherein the combination of lycopene and of manganese is in the form of a cosmetic composition or in the form of two separate cosmetic compositions,
said composition or compositions being in the form chosen from soft capsules, banded capsules, gels, dry or liquid emulsions, tablets, powders to be diluted, orodispersible powders, oils and drinkable ampoules, wherein the amounts of the lycopene and manganese provide a synergistic effect on the expression of SPRR2D in vitro and wherein the composition does not or compositions do not contain Vitamin C.

2. The cosmetic method according to claim 1, wherein the reinforcing the barrier function of the skin is to reduce a cutaneous discomfort of skin.

3. The cosmetic method according to claim 2, wherein the cutaneous discomfort is characterized by tautness, tingling, heating and/or itching.

4. The cosmetic method according to claim 1, wherein the reinforcing the barrier function of the skin is to improve the state of hydration of the skin.

5. The cosmetic method according to claim 1, wherein the molar ratio of lycopene over manganese in the composition is between 1/10 and 10/1.

6. The cosmetic method according to claim 1, wherein the lycopene used comes from a lycopene-rich tomato extract.

7. The cosmetic method according to claim 1, wherein the manganese is in the form of an inorganic manganese salt.

8. The cosmetic method according to claim 1 to reinforce the barrier function of the skin, wherein the administering of the combination of lycopene and of manganese is simultaneous.

9. The cosmetic method according to claim 1, wherein said administration is daily for a period of 1 to 16 weeks.

10. The cosmetic method according to claim 1, wherein the molar ratio of lycopene over manganese in the composition is between 1/5 and 5/1.

11. A cosmetic method to reinforce the protection of the skin with regards to external aggressions comprising at least one step of administering, simultaneously, separately or sequentially, to an individual by oral route of a combination of lycopene and manganese as agents to reinforce the protection of the skin with regards to external aggressions,
wherein the combination of lycopene and of manganese is in the form of a cosmetic composition or in the form of separate cosmetic compositions,
said composition or compositions being in the form chosen from soft capsules, banded capsules, gels, dry or liquid emulsions, tablets, powders to be diluted, orodispersible powders, oils and drinkable ampoules, wherein the amounts of the lycopene and manganese provide a synergistic effect on the expression of SPRR2D in vitro and wherein the compositions not or compositions do not contain Vitamin C.

12. The cosmetic method according to claim 2, wherein the reinforcing of the protection of the skin with regards to external aggressions is to reduce a cutaneous discomfort of skin.

13. The cosmetic method according to claim 2, wherein the reinforcing of the protection of the skin with regards to external aggressions is to improve the state of hydration of the skin.

14. The cosmetic method according to claim 11, wherein the molar ratio of lycopene over manganese in the composition is between 1/10 and 10/1.

15. The cosmetic method according to claim 11, wherein the molar ratio of lycopene over manganese in the composition is between 1/5 and 5/1.

* * * * *